(12) United States Patent
Gallego et al.

(10) Patent No.: US 11,583,484 B2
(45) Date of Patent: Feb. 21, 2023

(54) SKIN CARE COMPOSITION FOR THE PERISTOMAL REGION

(71) Applicant: Coloplast A/S, Humlebaek (DK)

(72) Inventors: Monica Ramos Gallego, Copenhagen SV (DK); Anne Kathrine K. Sloth Overgaard, Virum (DK); Admira Morse, Copenhagen N (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 16/960,020

(22) PCT Filed: Dec. 20, 2018

(86) PCT No.: PCT/DK2018/050410
§ 371 (c)(1),
(2) Date: Jul. 3, 2020

(87) PCT Pub. No.: WO2019/134726
PCT Pub. Date: Jul. 11, 2019

(65) Prior Publication Data
US 2021/0059912 A1    Mar. 4, 2021

(51) Int. Cl.
*A61K 8/25* (2006.01)
*A61K 45/06* (2006.01)
*A61Q 19/00* (2006.01)
*A61K 8/73* (2006.01)

(52) U.S. Cl.
CPC .............. *A61K 8/25* (2013.01); *A61K 8/732* (2013.01)

(58) Field of Classification Search
CPC .... A61K 2300/00; A61K 9/06; A61K 9/0014; A61K 9/0031; A61K 2800/10; A61K 8/25; A61K 8/732; A61K 8/8111; A61K 8/347; A61L 2400/14; A61L 15/60; A61P 17/02; A61P 17/00; A61Q 19/00
See application file for complete search history.

(56) References Cited

U.S. PATENT DOCUMENTS

| | | | |
|---|---|---|---|
| 5,869,033 A * | 2/1999 | Schulz | A61L 15/18 424/78.02 |
| 6,080,708 A | 6/2000 | Glenn, Jr. et al. | |
| 6,888,042 B1 * | 5/2005 | Freeman | A61F 13/0203 602/41 |
| 2002/0065354 A1 * | 5/2002 | Schnell | C11D 3/1253 524/492 |
| 2007/0020342 A1 * | 1/2007 | Modak | A61K 8/27 424/642 |
| 2008/0226698 A1 | 9/2008 | Tang et al. | |
| 2013/0101541 A1 * | 4/2013 | Kapsner | A61K 8/92 424/70.1 |
| 2016/0287493 A1 * | 10/2016 | Agarwal | A61K 8/731 |

FOREIGN PATENT DOCUMENTS

| | | |
|---|---|---|
| CN | 1361702 A | 7/2002 |
| WO | 2017050992 A1 | 3/2017 |

OTHER PUBLICATIONS

Biesterfeld. Polybutenes. Date retrieved: Aug. 24, 2021. <https://www.biesterfeld.com/en/us/product/polybutenes/>. (Year: 2021).*
National Institute of Diabetes and Digestive and Kidney Diseases. Ostomy Surgery of the Bowel. Dec. 23, 2016. <https://www.niddk.nih.gov/health-information/digestive-diseases/ostomy-surgery-bowel>. (Year: 2016).*

* cited by examiner

*Primary Examiner* — Tracy Liu
(74) *Attorney, Agent, or Firm* — Coloplast Corp., Coloplast A/S; Nick Baumann

(57) ABSTRACT

A skincare composition is provided, which comprises at least one clay, at least one first binding agent; and at least one second binding agent. The composition is to be used in a peristomal environment, and provides neutralization of stomal output.

20 Claims, No Drawings

SKIN CARE COMPOSITION FOR THE PERISTOMAL REGION

TECHNICAL FIELD

A neutralizer composition is provided, which can neutralize enzymes in stomal output.

BACKGROUND

Ostomy patients often use skin care compositions, to treat or prevent damage to the peristomal skin. Skincare compositions may be incorporated into stomal devices, or be used as separate compositions e.g. in the form of lotions, creams or gels.

Stomal output contains enzymes, which are known to damage skin. Neutralizers have been developed which are capable of neutralizing (i.e. deactivating) enzyme activity. Enzyme neutralization is a process which interferes with enzyme activity. Enzyme neutralization can be induced by enzyme sequestration, in which enzymes are removed from a mixture e.g. by adsorption onto a surface.

The peristomal region is characterised by mechanical stress due to the movements of the patient as well as sweat and body heat. Additionally, stomal output provides an environment with low pH and high enzyme activity. Skincare compositions must be formulated to handle such environmental factors, while maintaining good skincare properties. Additionally, skincare compositions should avoid excessive absorption of water which might increase enzyme concentration in the output.

SUMMARY

A skincare composition is thus provided, comprising:
a. at least one clay,
b. at least one first binding agent, being a polyethylene glycol (PEG) polymer or co-polymer with a number average molecular weight ($M_n$) of less than 1300; and
c. at least one second binding agent, being a polybutene with a number average molecular weight ($M_n$) of less than 3000, such as less than 2500.

The use of a skincare composition as defined herein in a peristomal environment is also provided. A particular use of the skincare composition is for neutralizing enzyme activity, in particular trypsin activity.

A method for preventing skin damage and/or maceration is provided. A method for reducing enzymatic activity in output is provided.

An ostomy device comprising the skincare composition as defined herein is also provided. A baseplate for an ostomy device, comprising the skincare composition as defined herein, is provided.

DETAILED DISCLOSURE

A skincare composition is provided, comprising:
a. at least one clay,
b. at least one first binding agent, being a polyethylene glycol (PEG) polymer or co-polymer with MW of less than 1300; and
c. at least one second binding agent, being a polybutene with a number average molecular weight ($M_n$) of less than 2500.

When exposed to stomal output or water, the skincare composition generally releases the clay into the surroundings, where it can neutralize enzymes in the output. Importantly, the neutralizing properties of the clay are maintained, even after formulation with the binding agents and its subsequent release into the surroundings.

By "output" is meant the effluent from a stoma, being faeces and/or urine in a more or less viscous form, possibly together with mucins secreted from the epithelial layer of the alimentary canal. In the case of a colostomy, the output might be quite solid, whereas an ileostomy may produce more liquid output. The output may contain digestive fluids with enzymes and other components that may be aggressive to the skin and thus may cause maceration and contact dermatitis of the skin. The output may also comprise components which may attack and degrade the ostomy device itself, e.g. the adhesive.

All molecular weights given are number average molecular weight ($M_n$) in the unit of g/mol.

The skincare composition comprises at least one clay. The clay is a particulate phyllosilicate material. The clay may comprise charged alumosilicate layers and interlayer cations. The clay may be present in an amount of 20-80 weight %, such as 20-70 weight %, such as 20-50 weight %, or in an amount of 25-80 weight %, such as 25-70 weight %, such as 25-50 weight %, preferably 40-80 weight %, more preferably 50-65 weight % of the composition. The clay is suitably a smectite clay, preferably selected from the group consisting of montmorillonite, beidellite, nontronite, saponite and hectorite. The clay may be a hectorite-type smectite clay, preferably laponite, suitably with CAS no. 53320-86-8, CAS no. 64060-48-6 or combinations thereof. In chemical terms, the clay is suitably a lithium magnesium sodium silicate or a sodium magnesium fluorosilicate.

Laponite RD belongs to the BYK family of lithium magnesium sodium silicates, which is the international nomenclature of cosmetic ingredients (INCI) name, which includes also laponite XLG and D. The empirical formula for laponite RD is $Na^+_{0.7}[(Si_8Mg_{5.5}Li_{0.3})O_{20}(OH)_4]^{-0.7}$.

Laponite XL21 belongs to the INCI family of sodium magnesium fluorosilicate (CAS 64060-48-6). This material contains fluorine ($F^-$) additionally to hydroxyl groups ($OH^{31}$). The empirical formula for laponite XL21 is $Na^+0.7[(Si_8Mg_{5.5}Li_{0.3})O_{20}(OH)_{2.5}F_{1.5}]^{-0.7}$.

The clay is formulated with at least two binding agents, which work in tandem to ensure the correct consistency of the skincare composition, and simultaneously the release of active clay upon contact with stomal output. The skincare composition may be in the form of a powder, a dough or a fluid.

The skincare composition further comprises a first binding agent, being a polyethylene glycol (PEG) polymer or co-polymer with $M_n$ of less than 1300. The first binding agent has a $M_n$ of less than 1300, suitably less than 1000, such as less than 700, such as less than 500.

The first binding agent is present in an amount of 10-40 weight %, preferably 10-30 weight % of the composition. In one aspect, the first binding agent is polyethylene glycol (PEG). Suitably, the first binding agent is PEG 200.

The skincare composition further comprises at least one second binding agent, being a polybutene with $M_n$ of less than 2500. Suitably, the second binding agent has a $M_n$ of less than 2000, preferably less than 1500. In embodiments, the second binding agent has a $M_n$ of 1300-2100. Suitably, the second binding agent has a $M_n$ of at least 1000. The second binding agent may be present in an amount of 10-40 weight % preferably 20-30 weight % of the composition. The second binding agent may be a co-polymer of isobutene and butene.

Without being bound by theory, it is thought that the upper limit on the $M_n$ of the first and second binding agents ensure the correct viscosity of the composition, so that—once mixed—clay particles will remain distributed evenly in the composition without precipitating due to the effects of gravity.

Additionally, a relatively lower limit on the $M_n$ of the first and second binding agents ensures the correct availability, for instance provided by release, of clay particles and the desired miscibility of the composition.

The present inventors found that using a PEG polymer or copolymer with a $M_n$ below 1300 and a polybutene with an $M_n$ below 2500 as first and second binders resulted in a composition with a good viscosity and a suitable consistency. In particular, it was found that the composition was able to remain stable even when exposed to stomal output. And that the clay of the composition was sufficiently exposed and/or released to provide the desired neutralization of enzymatic activity. This is in contrast to results obtained by the present inventors with higher $M_n$ binding agents. Typically, such higher $M_n$ binding agents were found to delay or inhibit enzyme neutralization, possibly because of excessive binding of the clay.

The present composition, having the clay together with a PEG polymer or copolymer with a $M_n$ below 1300 and a polybutene with an $M_n$ below 2500 as first and second binders thus provides advantageous stability and neutralization properties.

The skincare composition is suitably non-adhesive, so that it does not interfere or adhere to other components of the ostomy device.

In embodiments, the skincare composition further comprises potato starch. In embodiments, the composition comprises 20-60 weight % potato starch, such as 25-50 weight %, or 20-30 weight %, or 40-50 weight %.

In one particular aspect, the skincare composition has the following composition:

a. 20-80 weight % clay;
b. 10-40 weight % first binding agent;
c. 10-40 weight % second binding agent wherein said clay, first binding agent and second binding agent are as defined above. In another particular aspect, the skincare composition has the following composition:

a. 50-65 weight % clay;
b. 15-25 weight % first binding agent;
c. 20-25 weight % second binding agent wherein said clay, first binding agent and second binding agent are as defined above.

In embodiments, the skincare composition comprises 18-35 weight % clay; and 1-20 weight % of a first binding agent, such as 2-10 weight % of a first binding agent; and 20-35 weight % of a second binding agent, such as 20-30 weight % of a second binding agent.

In embodiments, the skincare composition comprises 18-35 weight % clay; and 1-20 weight % of a first binding agent, such as 2-10 weight % of a first binding agent; and 20-35 weight % of a second binding agent, such as 20-30 weight % of a second binding agent; and 20-60 weight % of potato starch, such as 25-50 weight % of potato starch.

The skincare composition may have one of the following compositions a-i:

| Composition | Clay (weight %) | First binding agent (weight %) | Second binding agent (weight %) |
|---|---|---|---|
| a. | 65 | 10 | 25 |
| b. | 65 | 25 | 10 |
| c. | 50 | 25 | 25 |
| d. | 60 | 20 | 20 |
| e. | 50 | 40 | 10 |
| f. | 80 | 10 | 10 |
| g. | 65 | 25 | 10 |
| h. | 50 | 10 | 40 |
| i. | 63 | 15 | 22 |

Also provided is the use of a skincare composition as described herein in a peristomal environment. The skincare composition is used for neutralizing enzyme activity, in particular trypsin activity. As mentioned, particles of clay are released from the skincare composition.

A method for reducing enzymatic activity in output is provided. The method comprises the steps of providing a skincare composition as defined herein and applying the skincare composition to peristomal skin and/or to an ostomy wafer. Hereby, the skincare composition is allowed to neutralize enzyme activity in any output that comes into contact with the composition.

A method for preventing skin damage and/or maceration is provided. The method comprises the steps of providing a skincare composition as defined herein and applying the skincare composition to peristomal skin and/or to an ostomy wafer. Hereby, the skincare composition is allowed to neutralize enzyme activity in any output that might come into contact with the peristomal skin, thereby reducing the aggressiveness of the output and preventing skin damage.

An ostomy device is also provided comprising the skincare composition described herein, as well as a baseplate for an ostomy device, comprising the skincare composition described herein.

The invention claimed is:

1. A skincare composition, comprising:
   a. at least one clay comprising one of $Na^+_{0.7}[(S_8Mg_{5.5}Li_{0.3})O_{20}(OH)_4]^{-0.7}$ and/or $Na^+0.7[(Si_8Mg_{5.5}Li_{0.3})O_{20}(OH)_{2.5}F_{1.5}]^{-0.7}$, wherein the clay is present in an amount of 20-80 weight % of the composition;
   b. at least one first binding agent, being a polyethylene glycol (PEG) polymer or co-polymer with $M_n$ of less than 1300, wherein the first binding agent is present in an amount of 10-40 weight % of the composition; and
   c. at least one second binding agent, being a polybutene with $M_n$ of less than 2500, wherein the second binding agent is present in an amount of 10-40 weight % of the composition.

2. The skincare composition according to claim 1, wherein the first binding agent has Mn of less than 1000.

3. The skincare composition according to claim 1, wherein the first binding agent is polyethylene glycol.

4. The skincare composition according to claim 1, wherein the second binding agent is a co-polymer of isobutene and butene.

5. The skincare composition according to claim 1, wherein the skincare composition further comprises potato starch.

6. A method to treat a skin surface in a peristomal environment comprising the step: applying a composition according to claim 1 to a peristomal environment wherein enzyme activity is neutralized.

7. A method to treat a skin surface in a peristomal environment comprising the step: applying a composition according to claim 1 to a peristomal environment wherein trypsin activity is neutralized.

8. An ostomy device comprising the skincare composition according to claim 1.

9. A baseplate for an ostomy device comprising the skincare composition according to claim 1.

10. The skincare composition according to claim 1, wherein said clay is present in an amount of 40-80 weight % of the composition.

11. The skincare composition according to claim 1, wherein said clay is present in an amount of 50-65 weight % of the composition.

12. The skincare composition according to claim 1, wherein the first binding agent has a Mn of less than 500.

13. The skincare composition according to claim 1, wherein the second binding agent has a Mn of less than 1500.

14. The skincare composition according to claim 1, wherein the first binding agent is present in an amount of 15-25 weight % of the composition.

15. The skincare composition according to claim 1, wherein the second binding agent is present in an amount of 20-30 weight % of the composition.

16. The skincare composition according to claim 1, wherein the second binding agent is present in an amount of 20-25 weight % of the composition.

17. The skincare composition according to claim 1, wherein the polyethylene glycol is present in an amount of 15-25 weight % of the composition.

18. The skincare composition according to claim 1, wherein the polyethylene glycol (PEG) co-polymer is present in an amount of 15-25 weight % of the composition.

19. The skincare composition according to claim 4, wherein the co-polymer of isobutene and butane is present in an amount of 20-30 weight % of the composition.

20. The skincare composition according to claim 4, wherein the co-polymer of isobutene and butane is present in an amount of 20-25 weight % of the composition.

* * * * *

UNITED STATES PATENT AND TRADEMARK OFFICE
CERTIFICATE OF CORRECTION

PATENT NO. : 11,583,484 B2
APPLICATION NO. : 16/960020
DATED : February 21, 2023
INVENTOR(S) : Monica Ramos Gallego, Anne Kathrine K. Sloth Overgaard and Admira Morse It is certified that error appears in the above-identified patent and that said Letters Patent is hereby corrected as shown below:

In the Claims

At Column 4, Line 42, in Claim 1 that portion of the empirical formula reading [($S_8Mg_{5.5}$ should read --[($Si_8Mg_{5.5}$--; and Na+0.7 should read --$Na^+_{0.7}$--

Signed and Sealed this
Twentieth Day of February, 2024

Katherine Kelly Vidal
*Director of the United States Patent and Trademark Office*